United States Patent [19]

Kim et al.

[11] Patent Number: 5,486,199
[45] Date of Patent: Jan. 23, 1996

[54] SYSTEM AND METHOD FOR REDUCING FALSE POSITIVES IN ATRIAL FIBRILLATION DETECTION

[76] Inventors: Jaeho Kim, 13323 NE. 69th Way, Redmond, Wash. 98052; Harley G. White, 937-210th Ave. NE., Redmond, Wash. 98053

[21] Appl. No.: 278,055

[22] Filed: Jul. 20, 1994

[51] Int. Cl.$^6$ ............................................. A61N 1/39
[52] U.S. Cl. ............................................. 607/5; 128/705
[58] Field of Search ........................ 607/5, 4, 6; 128/705, 128/702

[56] References Cited

U.S. PATENT DOCUMENTS

| | | | |
|---|---|---|---|
| 5,190,034 | 3/1993 | Sholder | 607/5 |
| 5,267,559 | 12/1993 | Jin et al. | 607/5 |
| 5,330,504 | 7/1994 | Somerville et al. | 607/5 |

Primary Examiner—William E. Kamm
Assistant Examiner—Kennedy J. Schaetzle
Attorney, Agent, or Firm—Richard O. Gray, Jr.

[57] ABSTRACT

An implantable atrial defibrillator applies cardioverting electrical energy to the atria of a human heart in need of cardioversion after first determining if there is an absence of potential atrial fibrillation. A sensor associated with the atria of the heart senses activity of the heart and generates a cardiac signal and a first detector detects cardiac events from the cardiac signal. A second detector responsive to time spans between immediately successive detected cardiac events which are grater in duration than a preselected interval detects for an absence of potential atrial fibrillation. An atrial fibrillation detector detects for atrial fibrillation if the second detector fails to detect an absence of atrial fibrillation, and a cardiovertor applies cardioverting electrical energy to the atria when the atria are in fibrillation.

25 Claims, 1 Drawing Sheet

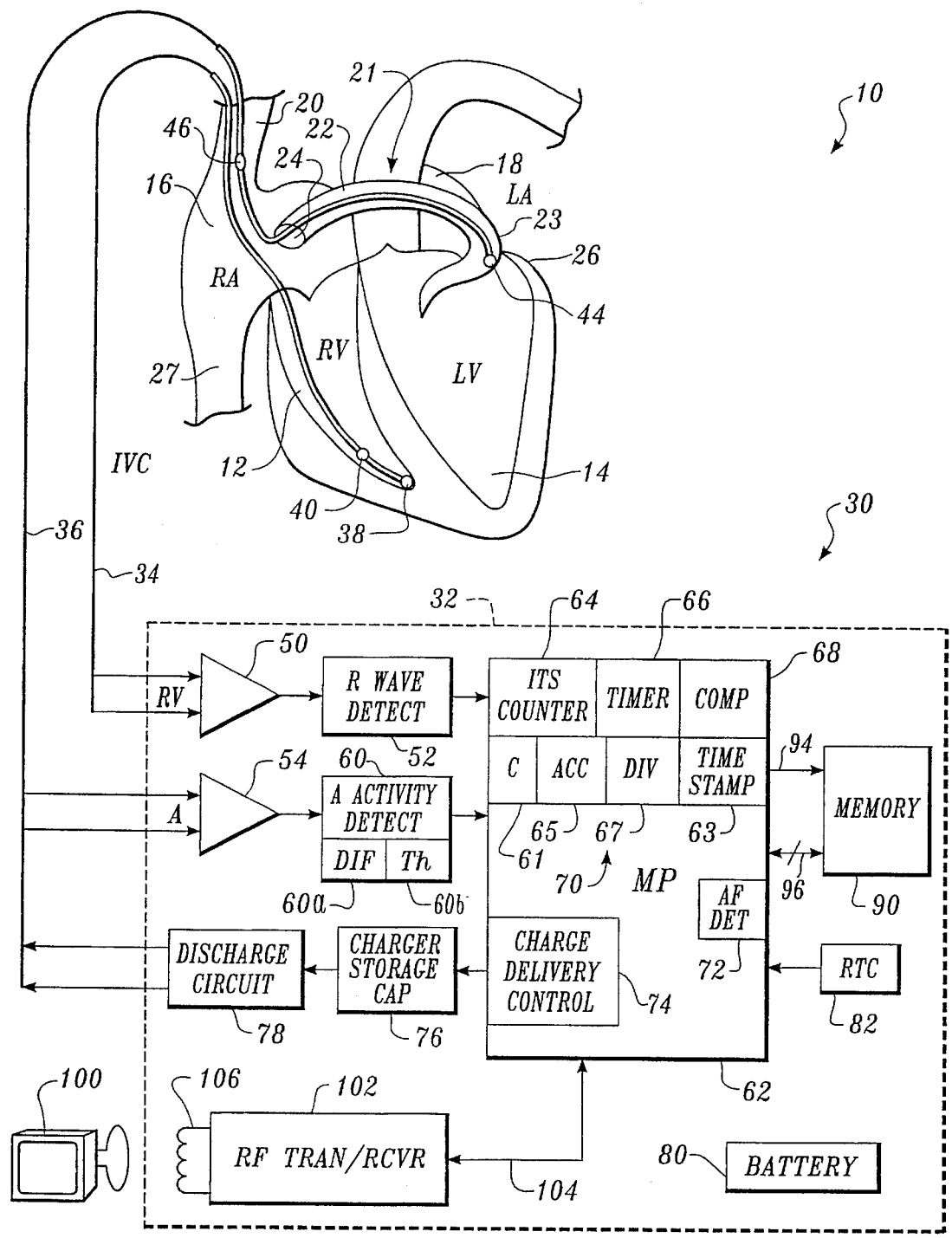

5,486,199

SYSTEM AND METHOD FOR REDUCING FALSE POSITIVES IN ATRIAL FIBRILLATION DETECTION

BACKGROUND OF THE INVENTION

The present invention generally relates to an atrial defibrillator and method for applying cardioverting electrical energy to the atria of a human heart in need of cardioversion. The present invention is more particularly directed to a system and method for use in an implantable atrial defibrillator for reducing false positives in the detection of atrial fibrillation. More specifically, the system and method of the present invention contemplates qualifying and accumulating time periods between cardiac events detected in an atrial channel during a cardiac signal acquisition period to determine if there is an absence of atrial fibrillation. If there is a failure to detect an absence of atrial fibrillation, an atrial fibrillation detector detects for atrial fibrillation.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

In order for an implantable atrial defibrillator to be truly automatic, it must include atrial fibrillation detection to determine if the atria are in fibrillation responsive to monitored activity of the heart. Atrial fibrillation detection must be both sensitive and specific. It must be sensitive so as to not miss an atrial fibrillation episode and specific so as to not misdiagnose a non-atrial fibrillation rhythm as atrial fibrillation. The latter mentioned misdiagnosis is referred to in the art as a false positive, and results in the patient receiving a cardioverting shock when such a shock is not needed.

False positives can impose undesirable consequences. If cardioverting energy is delivered when it is not needed, the patient obviously will experience unnecessary discomfort and inconvenience. Further, such unnecessary cardioverting energy deliveries will accelerate the depletion of the defibrillator battery and hence require early replacement of the defibrillator.

False positives have not been of much concern in the art because the only commercial defibrillators to date have been ventricular defibrillators for treating ventricular fibrillation. Ventricular fibrillation is a life threatening arrhythmia and, as a result, it is generally considered best to tolerate a low percentage of false positives and, to be on the safe side, in providing intervention.

Since the most common rhythm that occurs during the detection for atrial fibrillation is normal sinus rhythm, false positives may be reduced by employing atrial fibrillation detection which is specific to normal sinus rhythm, rejecting this rhythm as not atrial fibrillation. Also, since cardiac activity is generally disorganized and at a high rate during atrial fibrillation, false positives may be further reduced by employing atrial fibrillation detection which is also specific to organized rhythms of relatively low rate. To assure that an atrial fibrillation episode is not mistaken for a non-atrial fibrillation episode, the atrial fibrillation detection should also preferably be sensitive to atrial fibrillation. With this combination, effective atrial fibrillation detection with minimized false positives may be achieved.

Hence, there is a need in the art for an improved atrial fibrillation detection system and method which reduces the potential for false positives in detection of atrial fibrillation. The present invention provides such an improved system and method for use in atrial fibrillation detection which not only is specific to non-potential atrial fibrillation, but which is also sensitive to atrial fibrillation.

SUMMARY OF THE INVENTION

The present invention therefore provides a system for use in an implantable atrial defibrillator for reducing false positives in the detection of atrial fibrillation. The system includes sensing means associated with the atria of the heart for sensing activity of the heart and generating a cardiac signal, a first detector responsive to the cardiac signal for detecting cardiac events, and a second detector responsive to the first detector and time spans between immediately successive detected cardiac events which are greater in duration than a preselected interval for detecting an absence of potential atrial fibrillation.

In accordance with one aspect of the present invention, the sensing means associated with the atria of the heart senses activity of the heart and generates the cardiac signal during a preselected total time span. Also, the second detector may include a timer for timing the time span between immediately successive detected cardiac events, an accumulator for accumulating the time spans which are greater in duration than the preselected interval for generating an accumulated time span, and means for indicating the absence of potential fibrillation when the accumulated time span is greater than a preselected time period.

In accordance with a further aspect of the present invention, the sensing means associated with the atria of the heart senses activity of the heart and generates the cardiac signal during a plurality of cardiac cycles of the heart. Also, the second detector may include a first timer for timing the total time span of the plurality of cardiac cycles, a second timer for timing the time span between immediately successive detected cardiac events, an accumulator for accumulating the time spans which are greater in duration than the preselected interval for generating an accumulated time span, and means for indicating the absence of potential fibrillation when the accumulated time span is greater than a preselected fraction of the total time span.

The present invention further provides an implantable atrial defibrillator for applying cardioverting electrical energy to the atria of a human heart in need of cardioversion. The defibrillator includes sensing means associated with the atria of the heart for sensing activity of the heart and generating a cardiac signal, a first detector responsive to the cardiac signal for detecting cardiac events, and a second detector responsive to the first detector and time spans between immediately successive detected cardiac events which are greater in duration than a preselected interval for detecting an absence of potential atrial fibrillation. The defibrillator further includes an atrial fibrillation detector for detecting the presence of atrial fibrillation responsive to the second detector failing to detect an absence of potential atrial fibrillation, and cardioverting means for applying cardioverting electrical energy to the atria responsive to the atrial fibrillation detector detecting the presence of atrial fibrillation.

The present invention still further provides a method for reducing false positives in the detection of atrial fibrillation, including the steps of associating at least one electrode with at least one atrium of the heart, sensing electrical activity of the heart with the at least one electrode over a total time span to generate a cardiac signal, and detecting cardiac events from the cardiac signal. The method further includes the steps of timing the time span between immediately successive detected cardiac events, accumulating the time spans which are greater in duration than a preselected interval, and indicating the absence of potential atrial fibrillation when the accumulated time span is greater than a preselected fraction of the total time span.

The present invention still further provides a method for reducing false positives in the detection of atrial fibrillation, including the steps of associating at least one electrode with at least one atrium of the heart, sensing electrical activity of the heart with the at least one electrode over a total time span to generate a cardiac signal, detecting cardiac events from the cardiac signal, and indicating the absence of potential atrial fibrillation based upon time spans between immediately successive detected cardiac events which are greater in duration than a preselected interval.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole figure of which like reference numerals identify identical elements, and wherein the sole figure is a schematic block diagram of a fully implantable atrial defibrillator embodying the present invention for applying defibrillating electrical energy to the atria of a human heart and which is shown in association with the human heart in need of atrial fibrillation monitoring and potential cardioversion of the atria.

DETAILED DESCRIPTION OF THE PREFERRED EMBODIMENT

Prior to referring to the sole figure, a general description of a typical or normal cardiac cycle may be helpful in understanding the operation and various aspects of the present invention. The beginning of a cardiac cycle in normal sinus rhythm is initiated by a P wave which is normally a small positive wave. The P wave induces depolarization of the atria of the heart. Following the P wave there is a cardiac cycle portion which is substantially constant having a time duration on the order of, for example, 120 milliseconds.

The QRS complex of the cardiac cycle then normally occurs after the substantially constant portion. The dominating feature of the QRS complex is the R wave which is a rapid positive or negative deflection. The R wave generally has an amplitude greater than any other wave of the cardiac cycle and is characterized by a rapid deviation from and return toward baseline. The R wave is the depolarization of the ventricles and hence, as used herein, the term "ventricular activations" denotes R waves of the heart cardiac cycle. The QRS complex is completed by the S wave which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds. While the P wave in actuality initiates each new cardiac cycle, cardiac cycles are generally timed based upon detected R to R intervals because R wave detection is generally thought to be most reliable given the extreme amplitude and spiked shape of the R waves. Hence, as used herein, the term "cardiac cycle" is meant to denote the activity of the heart during immediately succeeding R waves.

The electrical activity of a heart experiencing atrial fibrillation as sensed in or near the atria is distinctly different than that for normal sinus rhythm. During normal sinus rhythm or other organized rhythms, there are discernible R and/or P waves and long portions of the cardiac cycles when there is little if any discernible atrial activity. In contrast, during atrial fibrillation, there are no discernible P waves and because the atria are in an unstable or fibrillating condition, there is detectable activity even during those portions of a cardiac cycle when there is little or no atrial activity during normal sinus rhythm or other organized rhythms. The present invention, as will be seen hereinafter, utilizes this difference between the electrical activity of the heart during atrial fibrillation and normal sinus rhythm, and other organized rhythms, as sensed in or near the atria to advantage for detecting the absence of potential atrial fibrillation to reduce the probability of false positives in atrial fibrillation detection.

Referring now to the sole figure, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in the sole figure are the right ventricle 12, the left ventricle 14, the right atrium 16, and left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an intravascular first lead 36, and an endocardial second lead 34. The enclosure 32 and first and second leads 36 and 34 are arranged to be implanted beneath the skin of a patient so as to render the atrial defibrillator 30 fully implantable.

The first lead 36 generally includes a first or tip electrode 44 and a second or proximal electrode 46. As illustrated, the second lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18.

The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy to the atria of the heart.

The second lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is fed through the superior vena cava 20, into the right atrium 16, and then into the right ventricle 12.

Within the enclosure 32, the atrial defibrillator 30 includes a first sense amplifier 54, an atrial activity detector 60, a second sense amplifier 50, and an R wave detector 52. The first sense amplifier 54 forms a first sensing means which together with electrodes 44 and 46 of the first lead 36 to which sense amplifier 54 is coupled, senses cardiac activity of the heart in or near the atria 16 and 18 and provides a cardiac signal to the atrial activity detector 60. The sense amplifier 50 forms a second sensing means which, together with electrodes 38 and 40 of the second lead 34 to which it is coupled senses cardiac activity in the right ventricle of the heart to provide a second cardiac signal to the R wave detector 52. Preferably both the sense amplifier 54 and the sense amplifier 50 include a differentiating filter so that the first cardiac signal provided by sense amplifier 54 and the second cardiac signal provided by sense amplifier 50 are differentiated first and second cardiac signals respectively.

The R wave detector 52 provides one or more output pulses for each R wave sensed during a cardiac cycle of the heart. To that end, the R wave detector may include a further differentiating filter for differentiating the differentiated second cardiac signal provided by sense amplifier 50 resulting in a twice differentiated second cardiac signal. The R wave detector 52 may further include a threshold circuit for setting an upper and lower threshold which provides an output when the twice differentiated second cardiac signal transitions beyond either the upper or lower thresholds.

Finally, the R wave detector preferably further includes an output pulse rate limiter having a programmable pulse repetition time interval. The pulse repetition time interval limits the number of output pulses issued for each detected R wave. It also allows one such pulse to indicate the completion of each detected R wave so that the end of each R wave may be determined. As an example, the repetition time interval may be eight milliseconds.

The atrial activity detector 60 preferably also includes a differentiating filter 60a for differentiating the differentiated first cardiac signal provided by sense amplifier 54 to provide a twice differentiated first cardiac signal and a threshold circuit 60b for setting an upper and lower threshold to provide an output when the twice differentiated first cardiac signal transitions beyond either the upper or lower threshold. The atrial activity detector 60 also preferably includes an output pulse rate limiter (not shown). The repetition time interval of this limiter is also preferably programmable and set to, for example, eight milliseconds. Each output of the detector 60 is treated as a separate cardiac event. However, as will be appreciated from the foregoing, there is not necessarily a one-to-one correlation between physiologic atrial events and individual outputs of the detector 60.

The enclosure 32 of the atrial defibrillator 30 further includes a microprocessor 62. The microprocessor 62 is preferably implemented in accordance with this embodiment of the present invention to result in a plurality of functional stages. The stages include a counter 61, a time stamp stage 63, a total time span timer 64, an accumulator 65, a further timer stage 66, a divider stage 67, and a comparator stage 68, all of which form atrial fibrillation absence detector 70 embodying the present invention. The stages further include an atrial fibrillation detector 72 and a charge delivery and energy control stage 74.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, such as a preselected time period, a preselected interval, or a preselected fraction to be referred to hereinafter, in the memory at the addresses defined by multiple-bit addresses conveyed over the address bus 94 by conveying the operating parameters and data to the memory 90 over the multiple-bit data bus 96. During a read operation, the microprocessor 62 obtains data or operating parameters from the memory at the storage locations identified by the multiple-bit addresses provided over the address bus 94 by receiving the operating parameters and data from the memory over the bi-directional data bus 96.

For entering operating parameters into the memory 90, the microprocessor 62 receives the operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or for receiving programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One preferred communication system is disclosed in copending U.S. application Ser. No. 08/001,330, filed Jan. 7, 1993 for "Telemetry System for an Implantable Cardiac Device", which application is assigned to the assignee of the present invention and incorporated herein by reference.

To complete the identification of the various structural elements within the enclosure 32, the atrial defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. Lastly, the defibrillator 30 includes a depletable power source 80, such as a lithium battery, for providing power to the electrical components of the atrial defibrillator 30, and a real time clock 82.

At spaced apart times, the real time clock 82 enables the microprocessor 62 which in turn enables the sense amplifiers 50 and 54, the R wave detector 52, and the atrial activity detector 60 to initiate a data acquisition period wherein a plurality of cardiac cycles of the heart are sensed. The data acquisition period is timed by the total time span timer 64 and preferably has a duration (total time span) of, for example, eight seconds. During the eight second data acquisition period, each output or burst of closely spaced outputs of the R wave detector 52, denoting the detection of an R wave, and each output of the atrial activity detector 60, denoting the detection of a cardiac event sensed by the electrodes 44 and 46 and sense amplifier 54, causes an interrupt to the microprocessor 62. Each interrupt is classified as either being a detected R wave or a detected cardiac event and time stamped by the time stamp stage 63. Each time stamp is then stored in the memory 90 according to its classification. After the eight second data acquisition period is completed, atrial fibrillation detection is commenced by the atrial fibrillation absence detector 70, determining if the atria 16 and 18 are not potentially in fibrillation in a manner to be described hereinafter and in accordance with this preferred embodiment of the present invention.

If the detector 70 detects an absence of potential atrial fibrillation, it terminates further atrial fibrillation detection. Rhythms which would be determined as non-potential atrial fibrillation include, for example, normal sinus rhythm, a low rate ventricular tachycardia, and heart block. However, if the detector 70 fails to detect an absence of potential atrial fibrillation, it causes the atrial fibrillation detector 72 to detect for atrial fibrillation from among the rhythms which would be considered as potential atrial fibrillation by the detector 70. Such rhythms, in addition to atrial fibrillation, may include, for example, atrial flutter, retrograde conduction due to ventricular tachycardia, intermittent runs of ventricular tachycardia, paroxysmal atria tachycardia, or a sinus tachycardia.

If the atrial fibrillation detector 72 determines that the atria are in fibrillation and thus in need of cardioversion, the charge delivery control 74 causes the charger and storage capacitor circuit 76 to charge the storage capacitor within the circuit 76 to a selected peak voltage. Thereafter, and in timed relation to a detected R wave, the atrial defibrillator 30, through the discharge circuit 78, applies a portion of the stored electrical energy to electrodes 44 and 46 and thus the atria 16 and 18 to cardiovert the atria 16 and 18.

In accordance with this preferred embodiment of the present invention, the detector 70 determines an absence of potential fibrillation of the atria in response to the time spans between immediately successive cardiac events detected by the atrial activity detector 60 which are greater in duration than a preselected interval. More specifically, after the eight second data acquisition is completed, the timer 66 determines the time spans between immediately successive cardiac events from the time stamps stored in memory 90. The time spans having a duration greater than a preselected interval, as for example, two hundred milliseconds (200 ms), are then added by the accumulator 65 to provide an accumulated time span. The comparator stage 68 then compares the accumulated time span to a preselected time period of, for example, two seconds. If the accumulated time span is equal to or greater than the preselected time period, the detector considers this to represent an absence of potential atrial fibrillation and terminates atrial fibrillation detection. However, if the accumulated time span is less than the preselected time period, the detector 70 considers this to represent potential atrial fibrillation and then causes the atrial fibrillation detector 72 to detect for the presence of atrial fibrillation. If the detector 72 determines that the atria are in fibrillation, cardioverting electrical energy is then applied to the atria as previously described.

In accordance with further aspects of the present invention, it is contemplated that the detector 70 may be operative for determining the absence of atrial fibrillation during the sensing of a plurality of cardiac cycles, for example, sixteen cardiac cycles. Here, data is acquired until a predetermined number of cardiac cycles, such as sixteen cardiac cycles, are sensed by the sense amplifier 50 and R wave detector 52, and counted by counter 61. The total time span timer times the total time span of the predetermined number of cardiac cycles. During the data acquisition, the timer 66 times the time span between immediately successive cardiac events and the accumulator 65 maintains a running accumulation of the time spans which are greater than a preselected interval of, for example, two hundred milliseconds (200 ms). At the end of the data acquisition, the divider stage 67 divides the accumulated time span provided by accumulator 65 by the total time span provided by the total time span timer 64. The comparator stage 68 then compares the result of the division to a preselected fraction. If the result of the division is equal to or greater than a preselected fraction, the detector considers that to represent an absence of potential atrial fibrillation. However, if the result is less than the preselected fraction, the detector 70 considers that to represent potential atrial fibrillation and will cause the detector 72 to detect for atrial fibrillation. In accordance with this preferred embodiment, the preselected fraction is preferably one-fourth (¼).

In accordance with either embodiment wherein the detector 70 determines if there is an absence of potential atrial fibrillation from data previously stored during the data acquisition period or from data as it is acquired during the data acquisition period, it is preferred that the atrial fibrillation detector 72, if required to detect for atrial fibrillation, detect for atrial fibrillation based on the data stored during the data acquisition period. In that manner, both detectors 70 and 72 will be operative upon data corresponding to the same heart activity. One such atrial fibrillation detector is disclosed in copending U.S. application Ser. No. 08/233,251, entitled "Selective Cardiac Activity Analysis Atrial Fibrillation Detection System and Method and Atrial Defibrillator Utilizing Same", filed Apr. 26, 1994, in the names of Harley White and Joe Bocek, which application is assigned to the assignee of the present invention and incorporated herein by reference. Briefly, as disclosed therein, from the stored data, and for each cardiac cycle of the plurality of cardiac cycles, a time for counting is established wherein each time for counting has a total duration less than the duration of its corresponding cardiac cycle. A counter counts the cardiac events detected by the detector during the time for counting of the plurality of cardiac cycles to provide a cardiac event count. A comparator compares the cardiac event count to a predetermined cardiac event count. If the cardiac event count is greater than the predetermined cardiac event count, the atria are deemed to be in fibrillation.

While a particular embodiment of the present invention has been shown and described, modifications may be made. For example, the cardiac events may be detected through slope detection or other means by which cardiac signal features varying in amplitude indicative of cardiac activity may be detected. It is therefore intended to cover in the appended claims all such changes and modifications which fall within the true spirit and scope of the invention.

What is claimed is:

1. A system for use in an implantable atrial defibrillator for reducing false positives in the detection of atrial fibrillation, said system comprising:

sensing means associated with the atria of the heart for sensing activity of the heart and generating a cardiac signal;

a first detector responsive to the cardiac signal for detecting cardiac events; and a second detector responsive to the first detector and time spans between immediately successive detected cardiac events which are greater in duration than a preselected interval for detecting an absence of potential atrial fibrillation.

2. A system as defined in claim 1 wherein the sensing means associated with the atria of the heart senses activity of the heart and generates the cardiac signal during a preselected total time span, and wherein the second detector includes a timer for timing the time span between immediately successive detected cardiac events, an accumulator for accumulating the time spans which are greater in duration than the preselected interval for generating an accumulated time span, and means for indicating the absence of potential fibrillation when the accumulated time span is greater than a preselected time period.

3. A system as defined in claim 2 wherein the preselected total time span is eight seconds.

4. A system as defined in claim 3 wherein the preselected time period is two seconds.

5. A system as defined in claim 2 wherein the preselected interval is two hundred milliseconds.

6. A system as defined in claim 1 wherein the sensing means associated with the atria of the heart senses activity of the heart and generates the cardiac signal during a plurality of cardiac cycles of the heart, and wherein the second detector includes a first timer for timing the total time span of the plurality of cardiac cycles, a second timer for timing the time span between immediately successive detected cardiac events, an accumulator for accumulating the time spans which are greater in duration than the preselected interval for generating an accumulated time span, and means for indicating the absence of potential fibrillation when the accumulated time span is greater than a preselected fraction of the total time span.

7. A system as defined in claim 6 wherein the plurality of cardiac cycles is on the order of sixteen cardiac cycles.

8. A system as defined in claim 6 wherein the preselected fraction is one-fourth.

9. A system as defined in claim 6 wherein the preselected interval is two hundred milliseconds.

10. A system as defined in claim 1 wherein said first detector includes a threshold detector.

11. An implantable atrial defibrillator for applying cardioverting electrical energy to the atria of a human heart in need of cardioversion, said defibrillator comprising:

sensing means associated with the atria of the heart for sensing activity of the heart and generating a cardiac signal;

a first detector responsive to the cardiac signal for detecting cardiac events;

a second detector responsive to the first detector and time spans between immediately successive detected cardiac events which are greater in duration than a preselected interval for detecting an absence of potential atrial fibrillation;

an atrial fibrillation detector for detecting the presence of atrial fibrillation responsive to the second detector failing to detect an absence of potential atrial fibrillation; and cardioverting means for applying cardioverting electrical energy to the atria responsive to the atrial fibrillation detector detecting the presence of atrial fibrillation.

12. An atrial defibrillator as defined in claim 11 wherein the sensing means associated with the atria of the heart senses activity of the heart and generates the cardiac signal during a preselected total time span, and wherein the second detector includes a timer for timing the time span between immediately successive detected cardiac events, an accumulator for accumulating the time spans which are greater in duration than the preselected interval for generating an accumulated time span, and means for enabling the atrial fibrillation detector when the accumulated time span is less than a preselected time period.

13. An atrial defibrillator as defined in claim 12 wherein the preselected time span is eight seconds.

14. An atrial defibrillator as defined in claim 13 wherein the preselected time period is two seconds.

15. An atrial defibrillator as defined in claim 12 wherein the preselected interval is two hundred milliseconds.

16. An atrial defibrillator as defined in claim 11 wherein the sensing means associated with the atria of the heart senses activity of the heart and generates the cardiac signal during a plurality of cardiac cycles of the heart and wherein the second detector includes a first timer for timing the total time span of the plurality of cardiac cycles, a second timer for timing the time span between immediately successive detected cardiac events, an accumulator for accumulating the time spans which are greater in duration than the preselected interval for generating an accumulated time span, and means for enabling the atrial fibrillation detector when the accumulated time span is less than a preselected fraction of the total time span.

17. An atrial defibrillator as defined in claim 16 wherein the plurality of cardiac cycles is on the order of sixteen cardiac cycles.

18. An atrial defibrillator as defined in claim 16 wherein said preselected fraction is one-fourth.

19. An atrial defibrillator as defined in claim 16 wherein said preselected interval is two hundred milliseconds.

20. An atrial defibrillator as defined in claim 11 wherein the first detector includes a threshold circuit.

21. A method for reducing false positives in the detection of atrial fibrillation, said method including the steps of:

associating at least one electrode with at least one atrium of the heart;

with the at least one electrode, sensing electrical activity of the heart over a total time span to generate a cardiac signal;

detecting cardiac events from the cardiac signal;

timing the time span between immediately successive detected cardiac events;

accumulating the time spans which are greater in duration than a preselected interval; and indicating the absence of potential atrial fibrillation when the accumulated time span is greater than a preselected fraction of the total time span.

22. A method as defined in claim 21 wherein the fraction is one-fourth.

23. A method as defined in claim 21 wherein the total time span is eight seconds.

24. A method as defined in claim 21 wherein the preselected interval is two hundred milliseconds.

25. A method for reducing false positives in the detection of atrial fibrillation, said method including the steps of:

associating at least one electrode with at least one atrium of the heart;

with the at least one electrode, sensing electrical activity of the heart over a total time span to generate a cardiac signal;

detecting cardiac events from the cardiac signal; and indicating the absence of potential atrial fibrillation based upon time spans between immediately successive detected cardiac events which are greater in duration than a preselected interval.

* * * * *